(12) United States Patent
Song et al.

(10) Patent No.: US 12,729,366 B2
(45) Date of Patent: Sep. 8, 2026

(54) CULTURE BROTH FOR GRAM-POSITIVE BACTERIA

(71) Applicant: QuantaMatrix Inc., Seoul (KR)

(72) Inventors: Seung Soo Song, Seoul (KR); Jin Ha Jeong, Seoul (KR); Gi Yoon Lee, Seoul (KR); Dong Young Kim, Seongnam-si (KR); Sang Kwon Han, Seoul (KR)

(73) Assignee: QuantaMatrix Inc., Seoul (KR)

( * ) Notice: Subject to any disclaimer, the term of this patent is extended or adjusted under 35 U.S.C. 154(b) by 637 days.

(21) Appl. No.: 17/640,965

(22) PCT Filed: Apr. 7, 2020

(86) PCT No.: PCT/KR2020/004682
§ 371 (c)(1),
(2) Date: Mar. 7, 2022

(87) PCT Pub. No.: WO2021/201328
PCT Pub. Date: Oct. 7, 2021

(65) Prior Publication Data

US 2022/0396760 A1 Dec. 15, 2022

(30) Foreign Application Priority Data

Apr. 3, 2020 (KR) ........................ 10-2020-0040669

(51) Int. Cl.
*C12N 1/20* (2026.01)
*C12R 1/46* (2006.01)

(52) U.S. Cl.
CPC ............ *C12N 1/20* (2013.01); *C12N 2500/30* (2013.01); *C12N 2500/70* (2013.01); *C12R 2001/46* (2021.05)

(58) Field of Classification Search
CPC .. C12N 1/20; C12N 2500/30; C12N 2500/70; C12R 2001/46
See application file for complete search history.

(56) References Cited

U.S. PATENT DOCUMENTS

2017/0037446 A1 2/2017 Sanhueza Chavez et al.
2019/0106724 A1 4/2019 Schuch
2020/0080128 A1 3/2020 Stern et al.

FOREIGN PATENT DOCUMENTS

JP 2019201654 A 11/2019
KR 20100030729 A 3/2010
(Continued)

OTHER PUBLICATIONS

Sanchez-Rozario, Y. and Johnson, M.D.L. (2021). Media Matters, Examining Historical and Modern *Streptococcus pneumoniae* Growth Media and the Experiments They Affect. Front. Cell. Infect. Microbiol. 11:613623. (Year: 2021).*

(Continued)

*Primary Examiner* — Daniel E Kolker
*Assistant Examiner* — Bailey M Morgan
(74) *Attorney, Agent, or Firm* — STIP Law Group, LLC

(57) ABSTRACT

The present invention relates to a culture broth for culturing Gram-positive bacteria that can simultaneously culture not only general Gram-positive bacteria but also *Streptococcus pneumoniae*. The present invention provides a culture broth for culturing Gram-positive bacteria, comprising a meat extract, casein hydrolysate, an antioxidant enzyme, a surfactant, starch, and a solidifying agent.

1 Claim, 4 Drawing Sheets

(56) References Cited

FOREIGN PATENT DOCUMENTS

| | | | |
|---|---|---|---|
| KR | 20120110292 | A | 10/2012 |
| KR | 20170007312 | A | 1/2017 |
| KR | 20210091512 | A | 7/2021 |

OTHER PUBLICATIONS

Clinical and Laboratory Standards Institute. (2012). Methods for Dilution Antimicrobial Susceptibility Tests for Bacteria That Grow Aerobically; Approved Standard (9th Edition). CLSI Document M07-A9. Clinical and Laboratory Standards Institute: Wayne, PA. (Year: 2012).*

Moreno et al. (1995). Immunocytochemical Localization of Catalase in the Central Nervous System of the Rat. J. Histochem. Cytochem. 43(12): 1253-1267. (Year: 1995).*

Pericone, et al. (2000). Inhibitory and Bactericidal Effects of Hydrogen Peroxide Production by *Streptococcus pneumoniae* on Other Inhabitants of the Upper Respiratory Tract. Infect. Immun. 68(7):3990-3997. (Year: 2000).*

Regev-Yochay et al. (2006). Interference between *Streptococcus pneumoniae* and *Staphylococcus aureus*: In Vitro Hydrogen Peroxide-Mediated Killing by *Streptococcus pneumoniae*. J. Bacteriol. 188(13):4996-5001. (Year: 2006).*

Sigma-Aldrich. C1345 Product Information. Accessed Sep. 16, 2024 from https://sigmaaldrich.com (Year: 2003).*

Sigma-Aldrich. 90922 Mueller Hinton Broth 2, Cation-Adjusted (M-H 2 Broth; Mueller Hinton II Broth). (Year: 2018).*

Agar et al. Erythrocyte Catalase; A Somatic Oxidant Defense? J. Clin. Invest. 1986, 77:319-321. (Year: 1986).*

Rennie et al., Factors Influencing Broth Microdilution Antimicrobial Susceptibility Test Results for Dalbavancin, a New Glycopeptide Agent, Journal of Clinical Microbiology, Oct. 2007, vol. 45, No. 10, pp. 3151-3154. (Year: 2007).*

International search report of PCT/KR2020/004682, Dec. 28, 2020, English translation.

Patricia A. Bradford et al., Tigecycline MIC Testing by Broth Dilution Requires Use of Fresh Medium or Addition of the Biocatalytic Oxygen-Reducing Reagent Oxyrase to Standardize the Test Method, Antimicrobial Agents and Chemotherapy, Oct. 2007, vol. 45, No. 9, pp. 3151-3154, American Society for Microbiology, Washington DC, USA.

Robert P. Rennie et al., Factors Influencing Broth Microdilution Antimicrobial Susceptibility Test Results for Dalbavancin, a New Glycopeptide Agent, Journal of Clinical Microbiology, Oct. 2007, vol. 45, No. 10, pp. 3151-3154, American Society for Microbiology, Washington DC, USA.

Seungsoo Song et al, Direct and rapid antimicrobial susceptibility testing of Streptococcus pneumoniae in the QMAC-dRAST system, ECCMID, Apr. 15, 2019, ECCMID, Amsterdam , Netherlands.

Seungsoo Song et al,Evaluation of Direct and Rapid Antimicrobial Susceptibility Testing for *Streptococcus pneumoniae* Using QMAC-dRAST system, QuantaMatrix, Jun. 2019, , Poster No. CPHM-839, ASM Microbe, San Francisco, USA.

ESCMID, European Congress of Clinical Microbiology and Infectious Diseases, Final Programme, Apr. 13-16, 2019, pp. 1-411, ECCMID, Amsterdam , Netherlands.

* cited by examiner

【Figure 1】
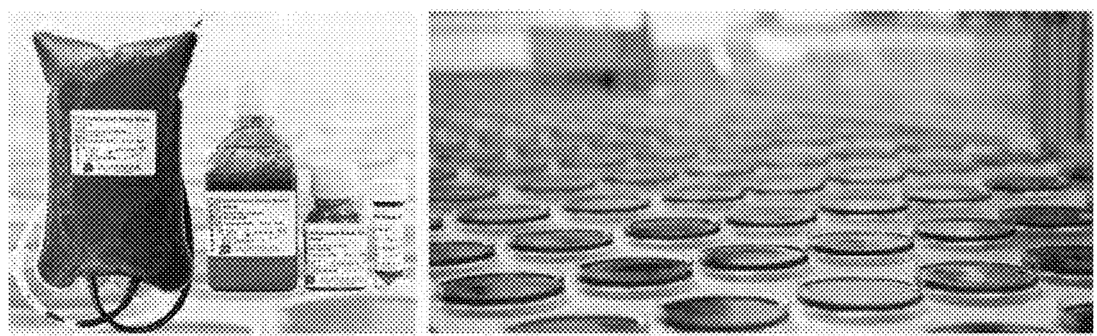
【Figure 2】
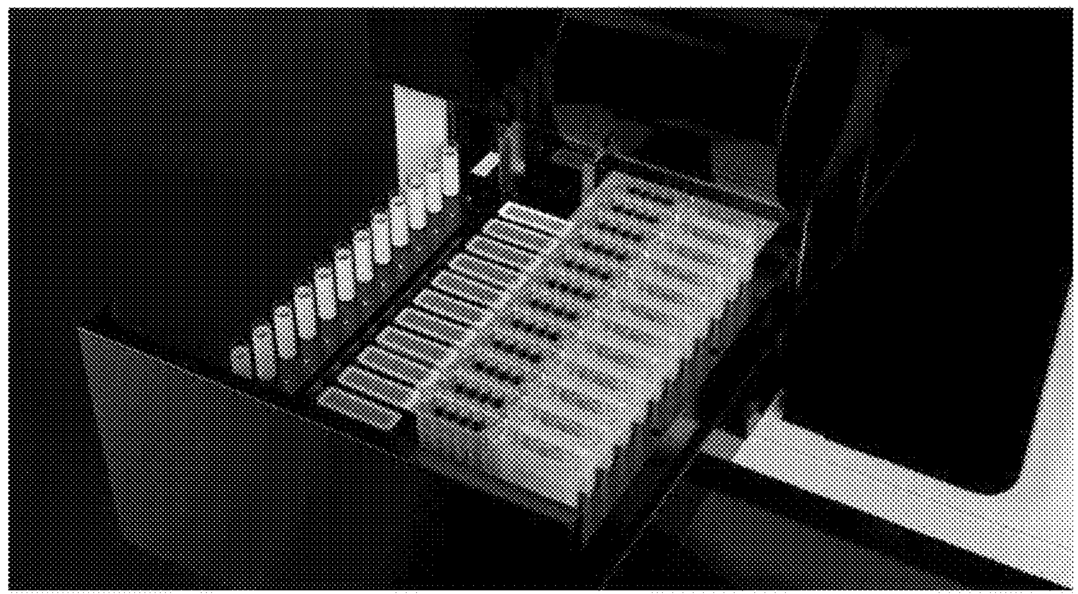

【Figure 3】
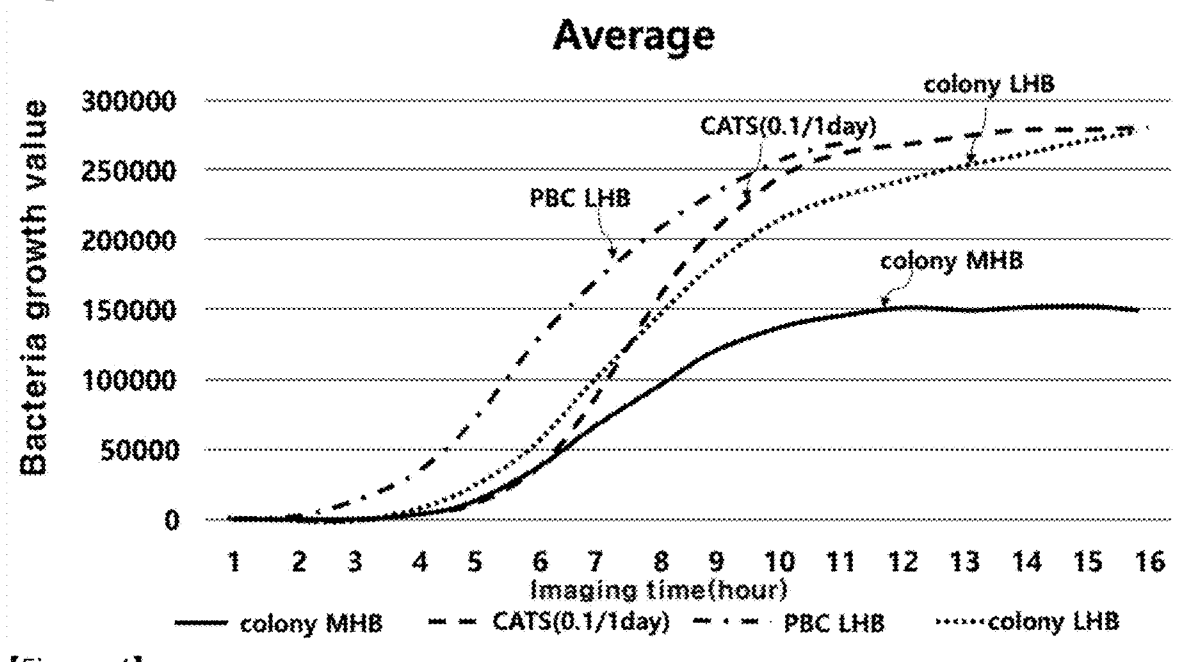
【Figure 4】
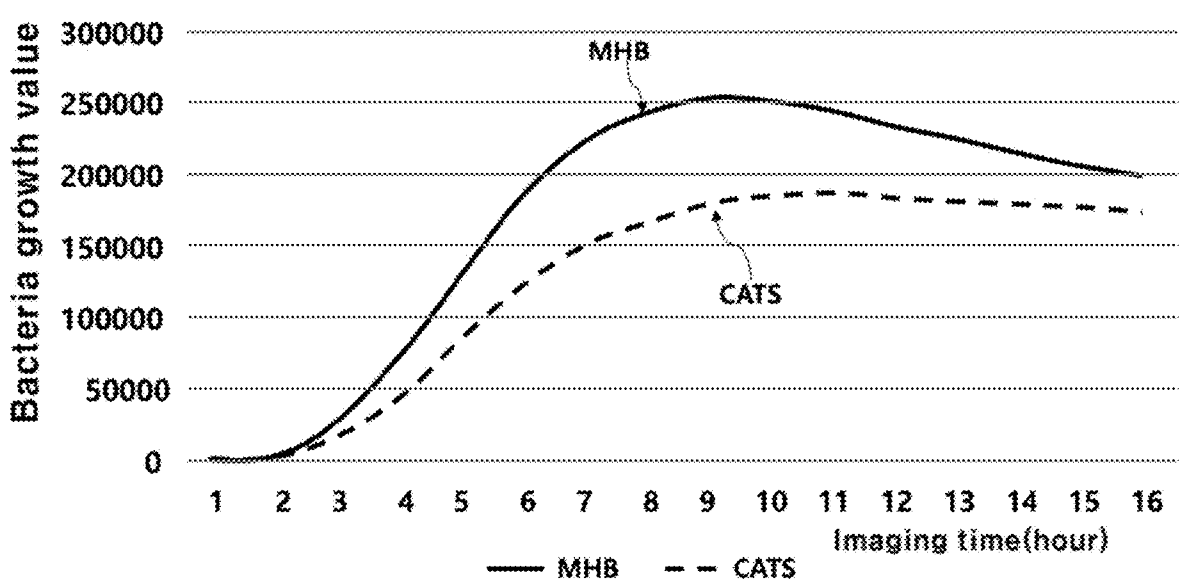

【Figure 5】
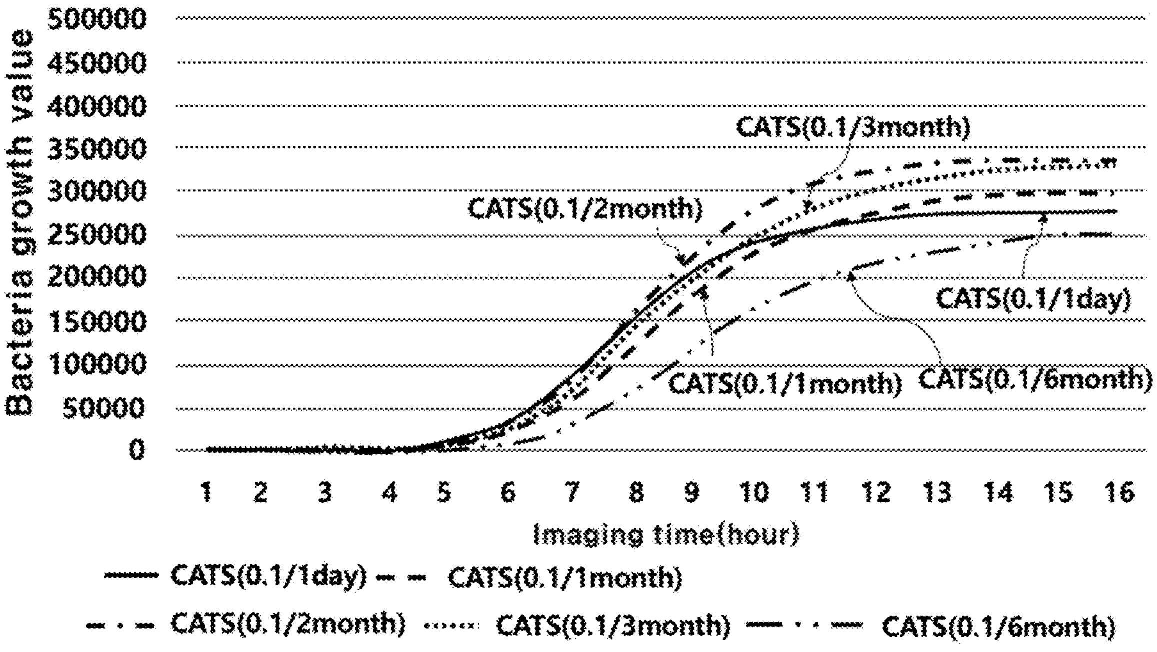
【Figure 6】
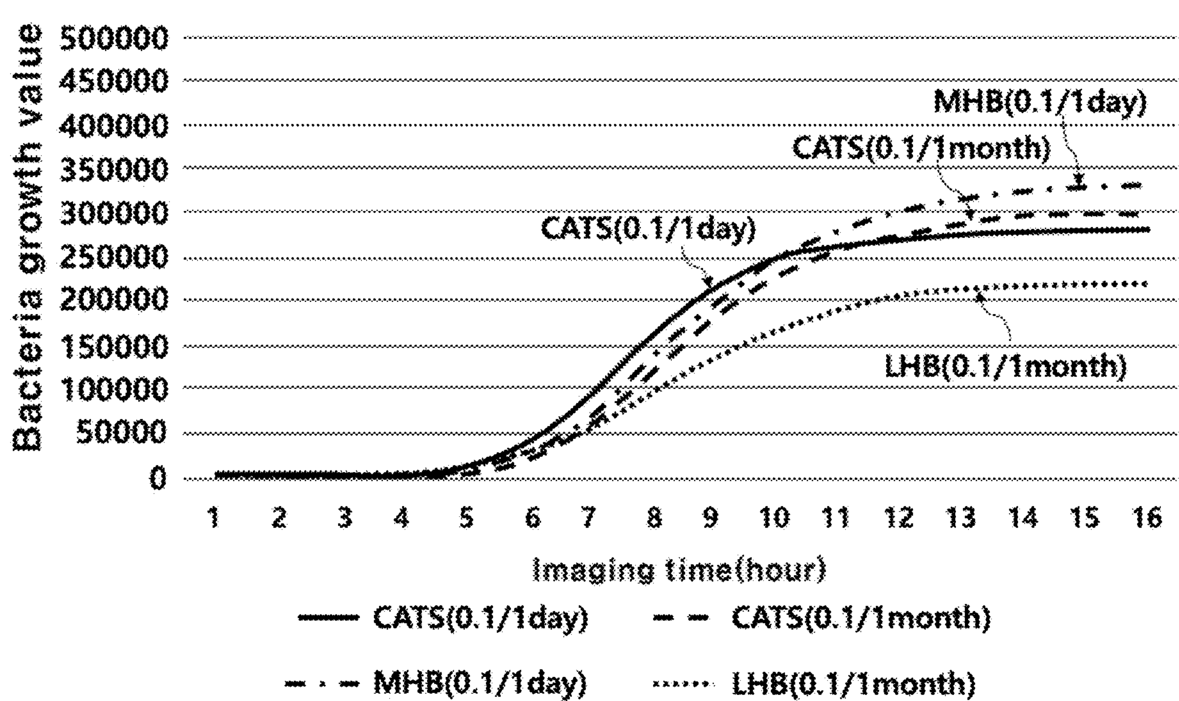

【Figure 7】
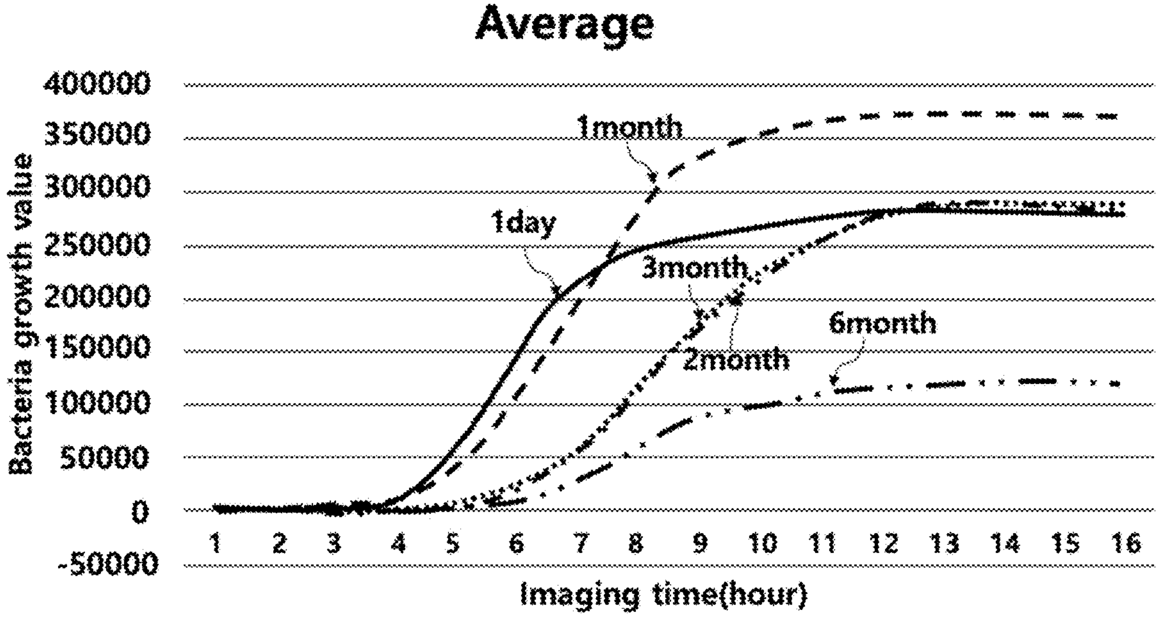
【Figure 8】
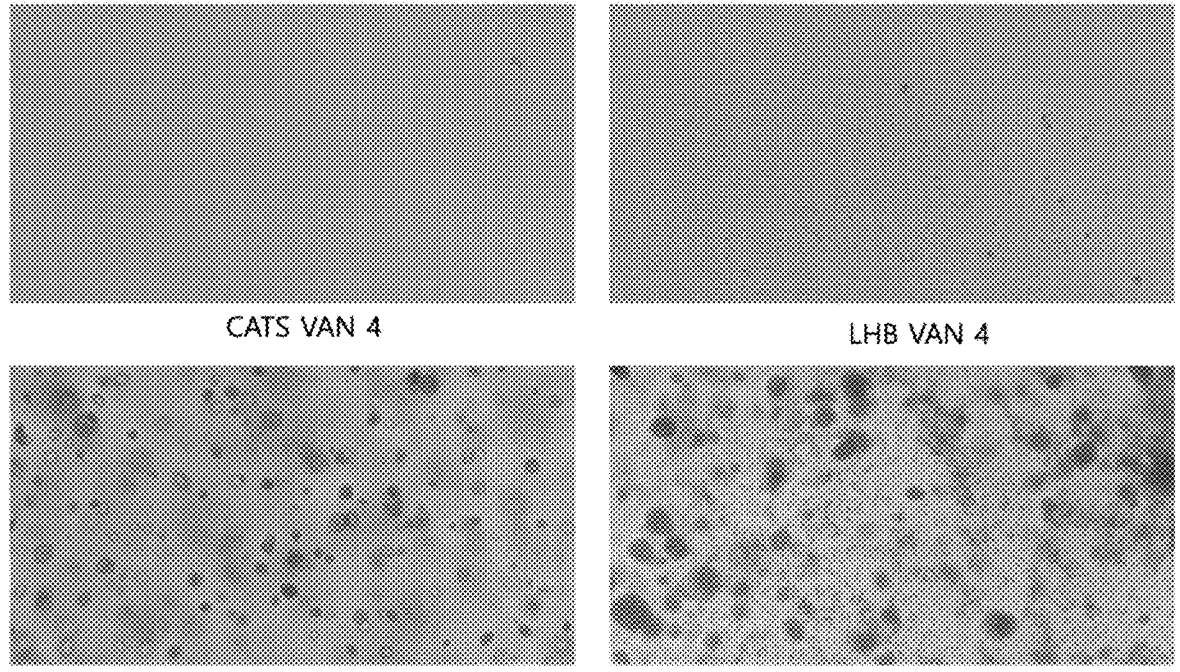

CULTURE BROTH FOR GRAM-POSITIVE BACTERIA

CROSS-REFERENCE TO RELATED APPLICATIONS

This application is the U.S. National Phase under 35 U.S.C. § 371 of International Application No. PCT/KR2020/004682 filed on Apr. 7, 2020, which in turn claims the benefit of Korean Application No. 10-2020-0040669 filed on Apr. 3, 2020, the disclosures of which are incorporated by reference into the present application.

TECHNICAL FIELD

The present invention relates to a culture broth for culturing Gram-positive bacteria, and more specifically, a culture broth for culturing Gram-positive bacteria capable of simultaneously culturing not only general Gram-positive bacteria but also *Streptococcus pneumoniae.*

BACKGROUND ART

Gram staining is the most important bacterial identification method that allows all bacteria to be broadly classified into two categories, and bacteria that are usually stained purple by the Gram staining are called Gram-positive bacteria, and bacteria that are not stained purple and are stained red by safranin, which is a contrast color, are called Gram-negative bacteria.

The Gram staining is performed by staining bacteria with crystal violet, then treating them with iodine, a mordant, and subjecting them to ethanol decolorization and counterstaining with safranin. Gram staining depends on the difference in the content of peptidoglycan in the cell wall, and it is known that general Gram-positive bacteria have a thick peptidoglycan layer on one cell membrane and Gram-negative bacteria have two cell membranes. The biggest reason for performing such Gram staining is that the culture method and antibiotics to be used vary depending on whether the Gram staining is positive or negative.

Gram-positive bacteria collectively refer to bacteria stained purple by such Gram staining, and include a peptidoglycan layer on the outer surface of the cell wall. As the Gram-positive bacteria, lactic acid bacteria, *Bacillus subtilis, Bacillus anthracis, Mycobacterium leprae, Staphylococcus, Corynebacterium diphtheriae, Streptococcus, Clostridium tetania, Actinomyces*, and the like are known. In contrast, as the Gram-negative bacteria, *Salmonella, Shigella, Salmonella typhi Escherichia coli Vibrio cholerae, Yersinia pestis, Neisseria gonorrhoeae, Neisseria meningitidis, Haemophilus pertussis*, and the like are known.

Beta-lactam antibiotics such as penicillin, glycopeptide antibiotics such as vancomycin, and macrolide antibiotics such as erythromycin are known to have high antimicrobial activity against Gram-positive bacteria, but aminoglycoside antibiotics with strong antibacterial activity against Gram-negative bacteria are known to have weak antibacterial activity against Gram-positive bacteria.

Mueller Hinton broth (MHB) is generally used for culturing Gram-positive bacteria for antibiotic susceptibility testing, but in the case of some Gram-positive bacteria, the growth of bacteria is slow in Mueller-Hinton broth (MHB), which does not have reactive oxygen species (ROS) enzyme, and thus, a culture medium different from that of general Gram-positive bacteria must be used.

*Streptococcus pneumoniae*, a type of representative Gram-positive bacteria not cultured with MHB, is the most common causative agent of not only community-acquired pneumonia, but also bacterial meningitis, otitis media, and sinusitis, and one of the most clinically important pathogens. Although penicillin resistance was first reported in clinical specimens in 1967, penicillin continued to be used as the first-line treatment for meningitis caused by *Streptococcus pneumoniae* without any problems. However, in the late 1970s, as intermediate- and high-resistant bacteria to penicillin appeared, cases of failure of penicillin treatment against *Streptococcus pneumoniae* began to be reported. Cases of unsuccessful treatment using broad-spectrum cephalosporins as a treatment for meningitis caused by resistant *Streptococcus pneumoniae* have also been reported, and strains showing resistance to quinolone antibacterial agents have also been reported. Therefore, in order to select the most effective therapeutic agent, a fast and accurate antimicrobial susceptibility test method is required.

Currently, the disc diffusion method using 1 g oxacillin disc is widely used as a screening test for penicillin susceptibility. However, this test alone has a limitation in that it cannot differentiate between an intermediate-resistant strain with a penicillin MIC of 0.12-1.0 g/mL and a resistant strain with a penicillin MIC of 2.0 g/mL or more. The liquid dilution method used to overcome this has high reliability, but has the disadvantages that the test process is complicated and takes a lot of time. On the other hand, the microbroth dilution panel of the conventional automated test equipment was also unable to perform *Streptococcus pneumoniae* susceptibility test due to the inappropriate composition and concentration of antibacterial agents. Recently, an E-test that can quickly and easily test the MIC for various antibacterial agents has been developed and is being used in some laboratories, but in the case of *Streptococcus pneumoniae*, which can be cultured only in a blood-based culture medium, the test must be performed separately from the existing Gram-positive bacteria, and thus, it has a problem in that the test period is long and additional costs are incurred.

In particular, as seen above, as *Streptococcus pneumoniae* is not cultured in MHB broth, which is a commonly used culture broth, a culture broth must be prepared separately, and since the thus prepared culture broth is based on animal blood, its storage period is very short, making it difficult to use in automated equipment, and thus, efforts to improve it are required.

DISCLOSURE

Technical Problem

In order to solve the above problems, the present invention is to provide a culture for culturing Gram-positive bacteria that may simultaneously culture not only general Gram-positive bacteria but also *Streptococcus pneumoniae.*

Technical Solution

In order to solve the above problems, the present invention provides a culture broth for culturing Gram-positive bacteria, comprising a meat extract, casein hydrolysate, an antioxidant enzyme, a surfactant, and starch.

In one embodiment, the culture broth may simultaneously culture *Streptococcus* and other Gram-positive bacteria.

In one embodiment, the *Streptococcus* may be *Streptococcus pneumoniae.*

In one embodiment, the antioxidant enzyme may be a catalase that converts reactive oxygen or hydrogen peroxide into oxygen.

In one embodiment, the catalase may be derived from bovine liver.

In one embodiment, the surfactant may be a nonionic surfactant.

In one embodiment, the meat extract may be a beef extract.

In one embodiment, the culture broth for culturing Gram-positive bacteria may contain 0.01 to 1 parts by weight of meat extract, 0.1 to 5 parts by weight of casein hydrolyzate, 0.01 to 0.5 parts by weight of catalase, 0.001 to 0.1 parts by weight of surfactant, and 0.01 to 1 parts by weight of starch based on 100 parts by weight of the culture broth.

Advantageous Effects

The culture broth for culturing Gram-positive bacteria according to the present invention may simultaneously culture not only Gram-positive bacteria, but also *Staphylococcus* and *Streptococcus pneumoniae*, unlike the conventional culture broth, and thus, it may be usefully used in an automated equipment that simultaneously performs multiple antibiotic tests.

In addition, the culture broth for culturing Gram-positive bacteria according to the present invention does not show a decrease in its performance even during long-term storage, unlike a blood-based culture broth, and thus, it may be usefully used as a raw material used in an automated equipment for antibiotic susceptibility test.

In addition, since the culture broth for culturing Gram-positive bacteria according to the present invention does not use a blood agent, foreign substances such as red blood cells and white blood cells contained in the blood agent are not observed, and thus, it may be usefully used for antibiotic susceptibility tests based on optical observation.

DESCRIPTION OF DRAWINGS

FIG. 1 shows a photograph of conventional horse lysed blood used in *Streptococcus pneumoniae* culture and a culture medium using the same.

FIG. 2 shows a photograph of a conventionally used automated diagnostic device, and is a photograph showing a culture broth, dry antibiotics and a pipette charged therein.

FIG. 3 is a graph showing the experimental results of the growth rate of *Streptococcus pneumoniae* according to one embodiment of the present invention.

FIG. 4 shows the experimental results of the growth rate of general Gram-positive bacteria according to one embodiment of the present invention.

FIG. 5 is a result of comparing the growth rate of bacteria according to the leaving period according to one embodiment of the present invention.

FIG. 6 is a graph comparing the growth rate of each medium after leaving for 1 month according to one embodiment of the present invention.

FIG. 7 is a graph showing the results of comparing the growth rate of LHB according to each leaving period according to one embodiment of the present invention.

FIG. 8 shows a photograph of the medium after leaving for a certain period of time according to one embodiment of the present invention.

BEST MODE

Hereinafter, preferred embodiments of the present invention will be described in detail. In describing the present invention, if it is judged that the specific description of the related known technologies may obscure the gist of the present invention, the detailed description thereof will be omitted. Throughout the specification, when a part "includes" an element, it means that other elements may be further included without excluding other elements, unless otherwise stated.

Since various modifications may be made to the present invention and the present invention may have various embodiments, specific embodiments will be illustrated and described in detail in the detailed description. However, this not intended to limit the present invention to specific embodiments, it is to be understood that this includes all modifications, equivalents, and substitutes included in the spirit and technical scope of the present invention.

However, the technology disclosed in the present specification is not limited to the embodiments described herein and may be embodied in other forms. However, the embodiments introduced herein are provided so that the disclosed content may be thorough and complete, and the technical spirit of the present technology may be sufficiently conveyed to those skilled in the art. In order to clearly express the elements of each device in the drawings, the dimensions of width, thickness, and the like of the elements are somewhat enlarged. In the description of the drawings, it was described from the viewpoint of the observer on the whole, and when an element is referred to as being positioned on another element, this includes both the meaning that an element may be positioned directly on another element, or an additional element may be interposed between the elements. In addition, a person having ordinary skill in the art will be able to implement the spirit of the present invention in various other forms within the scope without departing from the technical spirit of the present invention. In addition, the same reference numerals in the plurality of drawings refer to elements that are substantially the same as each other.

The terms used in the present invention are for the purpose of describing specific embodiment only and are not intended to limit the present invention. Singular expressions include plural expressions unless the context clearly indicates otherwise. In the present invention, terms such as "comprise," "have," and the like are intended to indicate that there is a feature, number, step, operation, component, part, or combination thereof described in the specification, and it should be understood that the terms do not exclude in advance the possibility of the presence or addition of one or more other features, numbers, steps, operations, components, parts, or combinations thereof.

On the other hand, the meaning of the terms described in this specification should be understood as follows. Terms such as "first," "second," and the like are for distinguishing one element from other elements, and the scope of rights should not be limited by these terms. For example, a first element may be termed a second element, and similarly, a second element may also be termed a first element.

In addition, the singular expression is to be understood as including the plural expression unless the context clearly dictates otherwise, and terms such as "comprise," "have," and the like are intended to indicate that there is a feature, number, step, operation, element, part, or combination thereof described, and it should be understood that the terms do not exclude in advance the possibility of the presence or addition of one or more other features, numbers, steps, operations, elements, parts, or combinations thereof. In addition, in performing the method or the manufacturing method, each process constituting the method may occur differently from the specified order unless a specific order is clearly described in context. That is, each process may occur in the same order as specified, may be performed substantially simultaneously, or may be performed in the reverse order.

The present invention is directed to a culture broth for culturing Gram-positive bacteria, comprising a meat extract, casein hydrolysate, an antioxidant enzyme, a surfactant, and starch.

The meat extract is used to supply protein, i.e., nitrogen and carbon to the culture broth, and extracts of cattle, pigs, sheep, chickens, or fish may be used. As the meat extract, an extract of animal muscle, fat, intestine, bone, or skin as described above may be used, but in order to increase the amount of protein extracted, an extract extracted from muscle may be preferably used. In addition, it is more preferable to use a beef extract having excellent long-term storage properties, easy culturing of various bacteria, and low fat content. The beef extract is prepared by extracting nutrients from the beef and then concentrating it, and a hot water extract of beef is generally used. In more detail, the fat is removed from the beef, and then the beef is cut to an appropriate size and the nutrient components contained in the beef are extracted by immersing it in water at 100° C. for 10 to 120 minutes. Next, a powdery product prepared by separating the liquid and concentrating the separated liquid is used. In this case, drying methods such as heating drying, drying under reduced pressure, or freeze drying may be used for the concentration, and it is preferable to use the final dried powder after sterilization to prevent contamination by other bacteria.

The meat extract may be included in an amount of 0.01 to 1 part by weight based on 100 parts by weight of the culture broth. When the meat extract is added in an amount of less than 0.01 parts by weight, the protein supply is not smooth, so it may be difficult to culture microorganisms, and when it is included in an amount of more than 1 part by weight, there is no further increase in the efficiency of microbial culture and the cost may be high.

The casein hydrolyzate refers to a product produced by hydrolyzing casein separated from milk, and is used for the purpose of supplying other types of protein that cannot be supplied from the meat extract. In general, it is preferable that the culture broth for culturing microorganisms is capable of uniformly culturing various microorganisms. However, it is difficult to culture a variety of microorganisms only with the meat extract, and accordingly, and thus, it is possible to prepare a culture broth for culturing microorganisms applicable to more diverse microorganisms by including the casein hydrolyzate.

The casein may be hydrolyzed by various methods, but it is preferably hydrolyzed by heating or hydrolyzed by adding an enzyme, and it is more preferable to hydrolyze by adding an enzyme to prevent denaturation of the protein by heat. Protease may be used as the enzyme used in this case, and pepsin, trypsin, chymotrypsin, or a mixture thereof may be used.

The casein hydrolyzate may be included in an amount of 0.1 to 5 parts by weight based on 100 parts by weight of the culture broth. When the casein hydrolyzate is included in an amount of less than 0.1 parts by weight, the protein to be supplied is reduced due to the casein, so it may not be easy to culture the microorganisms, and when it is included in an amount of more than 5 parts by weight, only the price of the culture broth may increase without further performance improvement.

The antioxidant enzyme is used to remove reactive oxygen or hydrogen peroxide generated during culturing microorganisms. General Gram-positive bacteria have enzymes for removing reactive oxygen species (ROS), so they are easy to culture in a medium, but Streptococci have a disadvantage in that they are difficult to culture in the conventional medium since they do not have an enzyme to remove reactive oxygen. In order to solve these problems, culture was performed using a blood agent containing horse or sheep blood. However, since blood agents are a kind of living tissue, their use period is short and storage is not easy, so they are mainly used in the disc diffusion method, and are used limitedly for automated test equipment. In particular, automated test equipment, which is essential for long-term storage of culture broth, has a disadvantage in that it is necessary to separately prepare a culture broth containing a blood agent for such Streptococci when testing for Gram-positive bacteria.

In addition, in the optical analysis method widely used in automated test equipment, the reliability of the analysis result may be lowered by various foreign substances included in the blood agent. Looking at this in detail, general blood agents may supply antioxidant enzymes necessary for culturing Streptococci, but in addition to antioxidant enzymes, but also contain cellular substances such as red blood cells, white blood cells, and platelets. Therefore, when the optical analysis method is used, the observation of the identification of the desired microorganism is hindered by the cellular substances such as red blood cells, white blood cells, and platelets contained in the blood, or the reliability of the test result may be lowered due to a malfunction of mistaking the cellular substance as a microorganism. In order to improve this, lysed blood (horse lysed blood, sheep lysed blood) is used, but as blood leaves a large amount of cellular debris after lysis, it does not improve the wrong results from the debris. Horse lysed blood used for culturing Streptococci was initially used for culturing Diphtheria (*Corynebacterium diphtheriae*) and is known to show faster growth when tellurite is removed from the medium. In addition, it is known that lysed blood elutes nicotinamide adenine dinucleotide from the ruptured red blood cells, thereby stimulating the growth of Influenza, Campylobacter, and the like. In the antibiotic susceptibility experiment, the reaction with trimethoprim and sulfonamide may be improved by adding the lysed horse blood to the medium. In addition, in culturing Streptococci, it may be cultured in the same medium as in Gram-positive bacteria by adding the lysed horse blood to the conventional medium.

The present invention may provide a culture broth for culturing Gram-positive bacteria that can be used in automated test equipment, as Streptococi; which do not produce an antioxidant enzyme, may be cultured simultaneously with Gram-positive bacteria and the shelf life of the culture broth may be greatly extended, by adding an antioxidant enzyme instead of such a blood agent.

As the antioxidant enzyme, superoxide dismutase (SOD), catalase, glutathione, vitamin C, vitamin E, or thiol, which are enzymes capable of removing reactive oxygen or hydrogen peroxide, may be used, but preferably catalase may be used.

Reactive oxygen or hydrogen peroxide is a substance pointed out as a cause of oxidizing cells to result in aging or death, and may act as a factor limiting the growth of microorganisms. Most microorganisms have antioxidant enzymes that can decompose such reactive oxygen or hydrogen peroxide as a kind of self-defense mechanism, as do Gram-positive bacteria. The antioxidant enzyme removes reactive oxygen and hydrogen peroxide through the following reaction.

$$2H_2O_2 \rightarrow 2H_2O+O_2$$

$$O^{2-}+H_2 \rightarrow H_2O \quad \text{[Formula 1]}$$

The catalase of the present invention is an enzyme for removing reactive oxygen or hydrogen peroxide, and can be synthesized by the liver of an animal or a microorganism. For the synthesis of such catalase, it is also prepared using a microorganism (bacteria or fungus), but preferably catalase derived from animal liver, more preferably catalase derived from liver of a cow that can be commercially produced can be used.

The method of producing catalase by microorganisms is a method of extracting catalase from microorganisms of the genus *Penicillium* such as *Penicillium chrysogenum* and *Penicillium notatum* and microorganisms such as *Aspergillus niger*, and although catalase with high enzymatic activity is being produced, it may be difficult to use in culture broth due to poor activity with Streptococci.

The method for extracting catalase from the liver of an animal is a method of preparing an enzyme solution by killing a mold by treatment with toluene, xylene, ethyl acetate, chloroform, or the like as a germicide and then extracting an enzyme by autolysis, recovering it by precipitation using acetone, ethanol, methanol, ammonium sulfate, or the like, and re-dissolving it in an aqueous solvent or water, and then removing the non-aqueous substances, and catalase extracted from bovine liver was composed of 4 subunits with a molecular weight of 250 kDa. In addition, it may be prepared through a method of preparing a water-soluble catalase enzyme solution by grinding the liver of an animal to extract an enzyme, recovering it by a crystallization method using acetone to dry it under reduced pressure, and then re-dissolving it in water to remove the insoluble substances, a method of preparing an enzyme solution by extraction using butanol as an organic solvent from the liver of an animal, and precipitation and crystallization with acetone, or through a method of preparing an enzyme solution by purification using a solvent such as ethanol from blood.

The catalase may have a composition of 2,000 to 60,000 unit/mg, and may be used as a dry powder or suspension. When the catalase has a composition of less than 2,000 units/mg, it is difficult to expect the reactive oxygen removal effect by the catalase, and the catalase having a composition of 60,000 units/mg or more does not improve its performance anymore and is not commercially available, so it is expensive to use, and thus, the test cost may increase. In addition, in the case of the dry powder, it is preferable to use freeze-drying rather than hot-air drying in order to prevent a decrease in the activity of the catalase due to heat during drying.

In addition, the catalase may be included in an amount of 0.001 to 0.075 parts by weight, preferably 0.005 parts by weight, based on 100 parts by weight of the culture broth. When the catalase is included in an amount of less than 0.01 parts by weight, it is difficult to expect an antioxidant effect, so simultaneous culture of Gram-positive bacteria and Streptococci may be difficult, and when it is included in an amount of more than 0.075 parts by weight, the culture rate may be reduced due to the excess enzyme.

The surfactant is added to maintain the stability and activity of the antioxidant enzyme, and a cationic surfactant, an anionic surfactant, or a nonionic surfactant may be used, preferably a nonionic surfactant may be used. When protein alone is present, protein aggregation may occur depending on the amount and passage of time. Proteins in which protein aggregation has occurred may be structurally modified without exposing the active surface and may lose their original ability. Surfactants have hydrophilic and hydrophobic surfaces, and when an appropriate concentration is applied to the protein as above, the surfactant interacts with the surface where the proteins aggregate and prevents the occurrence of protein aggregation. However, if the concentration of the surfactant is increased, the structure of the protein itself is released and the protein may lose its original function, so it is important to maintain an appropriate concentration.

The surfactant may be used in an amount of 0.001 to 0.03 parts by weight, preferably 0.01 parts by weight, based on 100 parts by weight of the culture broth. When the surfactant is added in an amount of less than 0.001 parts by weight, the increase in antioxidant enzyme activity by the surfactant does not occur, so the growth rate of *Streptococcus* may be slowed, and when it is added in an amount of more than 0.03 parts by weight, a phenomenon in which the structure of the protein is released due to excessive surfactant occurs, so the growth of the entire microorganism may be lowered.

The starch is included to adsorb toxins generated during culturing of microorganisms, and may prevent a decrease in the activity of antibiotics due to toxins. In particular, since the starch has little effect on the growth of microorganisms, it is possible to absorb toxins without interfering with the growth of microorganisms compared to other porous adsorbents. In addition, the starch may supply glucose to the culture broth. In the case of a microorganism that metabolizes glucose, since smooth culture may be difficult with only the meat extract, in this case, the starch may also be used as an energy source for supplying glucose to the microorganism. The starch is a plant-derived polysaccharide and may be hydrolyzed to provide glucose. In addition, the starch may act as a solidifying agent capable of increasing the viscosity of the medium through the pregelatinization or gelatinization process when the medium is prepared using the culture broth.

The starch may be included in an amount of 0.01 to 1 part by weight based on 100 parts by weight of the culture broth. When it is included in an amount of less than 0.01 part by weight, it is difficult to expect the microbial growth effect by starch, and when it is included in an amount of more than 1 part by weight, starch aggregates and causes defects in the culture broth, or the viscosity becomes too high during medium preparation, so it may be difficult to proceed with the experiment.

When the solidifying agent is included in the culture broth, a solid medium is prepared. When a liquid medium is used, the use of the solidifying agent is not required, but when a solid medium is used, it is preferable to add viscosity and elasticity to the medium by mixing the solidifying agent.

The solidifying agent may include one or more selected from agar, agarose, gelatin, alginate, collagen, or fibrin, and more preferably agar may be used. When a general medium is prepared, the culture broth and water are mixed, and then sterilized by heating to a certain temperature. In this case, the solidifying agent is dissolved in water as internal hydrogen bonds are broken by the supplied heat, and a flat surface is created due to surface tension. Thereafter, when heating is stopped and cooled, a medium having elasticity or viscoelasticity may be prepared by increasing the viscosity of the medium as the hydrogen bonds broken during heating are connected. Liquid medium is good for culturing microorganisms at a uniform concentration by the flow of microorganisms inside, but has the disadvantage that it is difficult to know the change of the effect at each point and to use the optical analysis method as the microorganisms are not fixed and move. Therefore, by using a medium having elasticity or viscoelasticity, it is possible to perform easy observation by minimizing the movement of microorganisms located inside or on the surface of the medium. In addition, the agar may be easily used as a solidifying agent since the antibiotic is easily diffused due to loose intermolecular bonds compared to other solidifying agents. The solidifying agent may be included in an amount of 0.1 to 5 parts by weight based on 100 parts by weight of the culture broth. When the solidifying agent is included in an amount of less than 0.1 parts by weight, it is difficult to conduct a smooth test as a medium with high fluidity is prepared due to insufficient solidification during medium preparation. when the solidifying agent is included in an amount of more than 5 parts by weight, the number of intermolecular bonds in the medium increases and the diffusion of the antibiotic becomes difficult, so the antibiotic susceptibility test cannot be performed.

In the present invention, the culture broth may simultaneously culture Streptococci and other Gram-positive bacteria. In the case of Mueller-Hinton medium, which is widely used as a culture broth for culturing Gram-positive bacteria in the conventional antibiotic susceptibility test, has the advantage capable of culturing various microorganisms including Gram-positive bacteria and Gram-negative bacteria due to its low selectivity for microorganisms. However, in the case of Mueller-Hinton medium, it was impossible to culture Streptococci, so simultaneous testing of Gram-positive bacteria and Streptococci was impossible. Therefore, it was inconvenient to separately prepare a medium containing lysed horse or sheep blood for culturing Streptococci. In addition, since the lysed horse or sheep blood is a biological material, the period for maintaining its quality is very short, from several days to several weeks, making it more difficult to use for automated test equipment that performs the test by loading the culture broth into the equipment. Therefore, there has been a waste of time and money since the test for Gram-positive bacteria must be performed during the antibiotic test and then the test for Streptococci must be performed again. However, by including antioxidant enzymes and surfactants, it is possible to simultaneously culture Streptococci and Gram-positive bacteria and the quality of the culture broth is maintained for more than 4 months, so the present invention may be usefully used in automated test equipment. In particular, it may be used to diagnose *Streptococcus pneumoniae*, which requires a lot of antibiotic susceptibility tests.

Hereinafter, preferred examples of the present invention will be described so that those of ordinary skill in the art can easily implement them with reference to the accompanying drawings. In addition, in describing the present invention, if it is determined that the specific description of the related known functions or known configurations may unnecessarily obscure the gist of the present invention, the detailed description thereof will be omitted. In addition, certain features presented in the drawings are enlarged, reduced, or simplified for ease of explanation, and the drawings and components are not necessarily drawn to scale. However, those skilled in the art will readily appreciate these details.

Example 1

2 g of beef extract powder, 17.5 g of casein hydrolyzate, and 1.5 g of starch were mixed, and then mixed with 900 mL of water to prepare a culture broth. The culture broth was sterilized under the conditions of 121° C. and 100 kPa to prepare an MHB medium. Next, 500 mg of lyophilized powder of bovine liver-derived catalase (C9322, Sigma-Aldrich®, 2,000 to 5,000 unit/mg, average molecular weight of 250 kDa) was dissolved in distilled water to remove foreign substances and then filtered. 1 g of nonionic surfactant (Sigma-Aldrich®, Pluronic® F-127) was also dissolved in distilled water and filtered. The preparation of the medium was completed by diluting the catalase solution and the surfactant solution in the previously prepared MHB medium.

Example 2

It was carried out in the same manner as in Example 1, except that 100 mg of catalase was used.

Example 3

It was carried out in the same manner as in Example 1, except that 750 mg of catalase was used.

Example 4

It was carried out in the same manner as in Example 1, except that Triton X-100 (Sigma-Aldrich) was used as the nonionic surfactant.

Example 5

It was carried out in the same manner as in Example 1, except that 0.1 g of the nonionic surfactant was used.

Example 6

It was carried out in the same manner as in Example 1, except that 3 g of the nonionic surfactant was used.

Comparative Example 1

It was carried out in the same manner as in Example 1, except that no catalase was used.

Comparative Example 2

It was carried out in the same manner as in Example 1, except that 1 g of catalase was used.

Comparative Example 3

It was carried out in the same manner as in Example 1, except that no surfactant was used.

Comparative Example 4

It was carried out in the same manner as in Example 1, except that 5 g of the nonionic surfactant was used.

Comparative Example 5

It was carried out in the same manner as in Example 1, except that Muller-Hinton medium (MHB) used for conventional culturing of Gram-positive bacteria was used as a medium.

Comparative Example 6

It was carried out in the same manner as in Example 1, except that a mixed medium of lysed horse blood (LHB) and Mueller-Hinton medium was used.

Experimental Example 1

The growth rate experiment of the medium prepared in Examples 1 to 6 and Comparative Examples 1 to 5 above was performed.

Agreement rates, error rates, and bacterial growth rates were compared using 30 samples of *Streptococcus pneumoniae* and 7 antibiotics (Levofloxacin, Linezolid, Penicillin, Tetracycline, Trimethoprim/sulfamethoxazole, Vancomycin, and Cefotaxime).

TABLE 1

| | EA | CA | VME | ME | mE |
|---|---|---|---|---|---|
| Example 1 | 92.1% | 97.9% | 0% | 0% | 2.1% |
| Example 2 | 82.2% | 80% | 1.1% | 0% | 3.6% |
| Example 3 | 87.8% | 98.1% | 2.4% | 0% | 1% |
| Example 4 | 89.8% | 97.3% | 0% | 0% | 2.7% |
| Example 5 | 87.8% | 86.5% | 3.3% | 0% | 3.9% |
| Example 6 | 82.1% | 81.4% | 4.6% | 0% | 2.6% |
| Comparative Example 1 | 65.7% | 75.4% | 4.7% | 4.9% | 8.4% |
| Comparative Example 2 | 82.4% | 91.5% | 1.5% | 0% | 3.1% |
| Comparative Example 3 | 78.4% | 75.7% | 3.6% | 1.1% | 1.5% |
| Comparative Example 4 | 69.8% | 74.1% | 4.5% | 2.3% | 4.7% |
| Comparative Example 5 | 68.1% | 76.4% | 4.9% | 5.4% | 7.5% |
| Comparative Example 6 | 83.3% | 92.4% | 0% | 1.7% | 1.4% |

In Table 1 above, EA stands for essential agreement and is an index comparing the MIC agreement rates when performing AST, and CA stands for categorical agreement and is an index comparing the SIR (interpretation) agreement rates when performing AST. ME stands for a major error and BMD represents a case that is susceptible (antibiotic sensitivity) but produces a result as resistance (antibiotic resistance) in the equipment to be compared, and VME stands for a very major error and BMD represents a case that is resistant (antibiotic resistance) but produces a result as susceptible (antibiotic sensitivity) in the equipment to be compared. mE stands for a minor error and indicates a case where the equipment to be compared is determined to be S or R when the BMD determines that it is I (intermediate), or a case where the equipment to be compared is determined to be I when the BMD determines that it is S or R.

As shown in Table 1, it could be confirmed that Examples 1 to 4 of the present invention exhibit a high agreement rate (82% or more). In particular, since the same or superior level of agreement as in Comparative Example 6 using a mixture of lysed horse blood (LHB) used in the past was shown, it was found that it could be used as a substitute for the conventional test method. However, it is judged that Comparative Examples 1 and 5, in which antioxidant enzymes were not used, have a lower agreement rate and are difficult to use in the test, and it could be confirmed that in the cases where the surfactant was not used (Comparative Example 3) or the surfactant was used excessively (Comparative Example 4), the agreement rate was lowered, and thus, it could be confirmed that the activity of the antioxidant enzyme was increased by the surfactant. it was confirmed that Comparative Example 2, in which the antioxidant enzyme was used excessively, was found to have a similar effect to the Examples, but the growth rate of the bacteria was reduced due to the excess antioxidant enzyme.

Also in the error rate, it was confirmed that the present invention showed significantly fewer test results showing a false negatives (VMEs) and hardly showed false positives (MEs), but Comparative Examples showed high false positives and also showed false negatives that could act as fatal results, indicating that only Examples of the present invention can be used for antibiotic susceptibility test.

In the case of the bacterial growth rate, the bacterial growth rate was not compared with the BMD results, but displayed as a graph of the bacteria growth value measured every hour in the dRAST equipment. As shown in FIG. 3, it could be confirmed that Example 1 (CATS) of the present invention showed the same or faster growth than the LHB used in the past, whereas MHB in which LHB was not used showed a very low growth rate.

That is, it was confirmed that the Examples of the present invention showed an agreement rate and growth rate of at least the same level as compared to Comparative Example 6 using LHB, but the Example of the present invention had higher productivity and stability.

Experimental Example 2

In order to confirm whether it can be used against other Gram-positive bacteria except for *Streptococcus*, an experiment was conducted to check the agreement rate, error rate, and growth rate of bacteria using 100 samples of selected Gram-positive bacteria (*Staphylococcus* spp. and *Enterococcus* spp.).

TABLE 2

| | EA | CA | VME | ME | mE |
|---|---|---|---|---|---|
| Example 1 | 96.1% | 95.8% | 2.9% | 0.5% | 1.5% |
| Example 2 | 91.3% | 91.1% | 2.1% | 0.2% | 1.6% |
| Example 3 | 95.4% | 97.1% | 2.5% | 0.1% | 1.4% |
| Example 4 | 94.3% | 97.4% | 1.1% | 0.4% | 2.1% |
| Example 5 | 96.7% | 89.7% | 3.9% | 0.6% | 1.7% |
| Example 6 | 93.1% | 89.4% | 4.1% | 0.1% | 2.0% |
| Comparative Example 5 | 96.3% | 96% | 4.7% | 1.2% | 1.5% |

As shown in Table 2, it was confirmed that the Examples according to the present invention did not have a significant difference or had a higher value than that of MHB. As shown in FIG. 4, in the case of growth rate, it was confirmed that the time to the value indicating the same degree of growth of the bacteria was found to be faster in the Examples, so a faster test was possible. Therefore, it was confirmed that the examples of the present invention could be used to replace the existing MHB.

Experimental Example 3

After leaving the prepared medium for a certain period of time (1 day, 1 month, 2 months, and 4 months), 30 samples of *Streptococcus pneumoniae* and 7 types of antibiotics were used to compare the agreement rate, error rate, and bacterial growth rate.

TABLE 3

| | EA | | | | CA | | | | VME | | | |
|---|---|---|---|---|---|---|---|---|---|---|---|---|
| | 1 day | 1 month | 2 months | 4 months | 1 day | 1 month | 2 months | 4 months | 1 day | 1 month | 2 months | 4 months |
| Example 1 | 87.2 | 91 | 93.6 | 92.6 | 97.9 | 94.8 | 98.6 | 97.9 | 0 | 3.2 | 0 | 0 |
| Example 2 | 82.2 | 83.4 | 83.1 | 83.0 | 80 | 81.4 | 81.1 | 80.9 | 1.1 | 0.3 | 3.0 | 0 |
| Example 3 | 87.8 | 87.7 | 88.4 | 87.1 | 98.1 | 98.0 | 97.4 | 97.4 | 2.4 | 0 | 0 | 1.1 |
| Example 4 | 89.8 | 89.7 | 89.1 | 87.8 | 97.3 | 97.1 | 97.2 | 97.1 | 0 | 0 | 0.9 | 1.4 |
| Example 5 | 87.8 | 87.1 | 87.4 | 87.5 | 86.5 | 87.1 | 89.1 | 85.4 | 3.3 | 2.7 | 2.1 | 2.8 |
| Example 6 | 82.1 | 82.5 | 81.4 | 81.5 | 81.4 | 81.6 | 81.4 | 81.0 | 4.6 | 4.1 | 3.9 | 3.4 |
| Comparative Example 6 | 90 | 89.3 | 88.1 | 86.2 | 98 | 96.6 | 94.1 | 95.1 | 2.5 | 3.7 | 11.1 | 8.6 |

| | ME | | | | mE | | | |
|---|---|---|---|---|---|---|---|---|
| | 1 day | 1 month | 2 months | 4 months | 1 day | 1 month | 2 months | 4 months |
| Example 1 | 0 | 0 | 0 | 0 | 2.1 | 4.4 | 1.4 | 2.1 |
| Example 2 | 0 | 0 | 0 | 0 | 3.6 | 3.7 | 3.4 | 3.6 |
| Example 3 | 0 | 0 | 0 | 0 | 1 | 1.1 | 1.1 | 0.7 |
| Example 4 | 0 | 0 | 0 | 0 | 2.7 | 1.7 | 1.5 | 3.1 |
| Example 5 | 0 | 0 | 0 | 0 | 3.9 | 3.8 | 3.1 | 3.1 |
| Example 6 | 0 | 0 | 0 | 0 | 2.6 | 3.4 | 2.4 | 2.1 |
| Comparative Example 6 | 0 | 0 | 0 | 0 | 1 | 2 | 1.5 | 1.5 |

As shown in Table 3, it could be confirmed that in Comparative Example 6 using the lysed horse blood, the performance deteriorated after one month had elapsed. In particular, a decrease in the agreement rate could be confirmed, and the false-positive rate was also increasing, indicating that the performance could no longer be maintained after one month had elapsed. However, it was confirmed that the Examples of the present invention maintained almost the same performance up to 4 months, and thus, it was confirmed that there was no problem in use as a medium even if stored for 4 months.

In addition, as shown in FIG. 8, it was confirmed that the observation of foreign substances was increased in some wells of Comparative Example 6, and it was confirmed that the color of the medium changed from bright red to brown over time. That is, it was confirmed that the lysed horse blood (LHB)-based medium used in the past had a very short storage period (within 1 month), and the examples of the present invention had the same or higher performance as the conventional MHB for Gram-positive bacteria and had the same performance as the blood-based medium (Comparative Example 6) for *Streptococcus pneumoniae*, and also had a higher preservation period.

In a growth rate comparison experiment to confirm the difference in long-term growth rates, growth rates were compared for 1, 2, 3, and 6 months. The growth rate was displayed as a graph of the bacterial growth value measured every hour in the dRAST equipment using Example 1 (CATS) of the present invention, Comparative Example 5 (MHB), and Comparative Example 6 (LHB). As shown in FIG. 5, it could be confirmed that when the medium according to Example 1 of the present invention was used, there was no significant difference in the growth rate even after the period had elapsed. As shown in FIG. 6, it could be confirmed that in the growth rate after 1 month, MHB was the lowest and LHB also decreased to a certain extent. However, it was confirmed that in the case of MHB, the growth rate was low even when time did not elapse as shown in FIG. 3, so there was no significant difference in the growth rate even when 1 month had elapsed, whereas in the case of LHB, although the growth rate was similar to that of the examples of the present invention in FIG. 3, the growth rate was decreased to a certain extent after one month had elapsed, thereby reducing the performance. In the growth rate experiment using LHB, it was confirmed that as shown in FIG. 7, the growth rate started to decrease after 3 months, and showed a very low growth rate after 6 months, so it was difficult to use as a medium due to its low activity.

As a specific part of the present invention has been described in detail above, it will be apparent to those skilled in the art that these specific descriptions are only preferred embodiments, and the scope of the present invention is not limited thereby. Accordingly, it is intended that the substantial scope of the present invention be defined by the appended claims and equivalents thereof.

The invention claimed is:

1. A culture broth for culturing Gram-positive bacteria, comprising:

a beef extract;

casein hydrolysate;

catalase derived from bovine liver and having an activity of at least 2,000 units/mg;

a nonionic surfactant; and starch, wherein, the culture broth is capable of cultivating *Streptococcus, Staphylococcus* spp., and *Enterococcus* spp., the culture broth comprises:

0.01 to 1 parts by weight of the beef extract, 0.1 to 5 parts by weight of the casein hydrolysate, 0.001 to 0.075 parts by weight of the catalase, 0.001 to 0.03 parts by weight of the nonionic surfactant, and 0.01 to 1 parts by weight of the starch, based on 100 parts by weight of the culture broth, the nonionic surfactant and catalase are present at a weight ratio from 0.2 to 10, the culture broth does not contain blood and/or lysed blood, and the culture broth is capable of cultivating *Streptococcus pneumoniae, Staphylococcus* spp., and *Enterococcus* spp.

* * * * *